(12) United States Patent  
Soon-Shiong et al.

(10) Patent No.: US 10,262,759 B2
(45) Date of Patent: Apr. 16, 2019

(54) PERSONAL HEALTH OPERATING SYSTEM

(71) Applicant: NANTHEALTH, INC., Culver City, CA (US)

(72) Inventors: Patrick Soon-Shiong, Culver City, CA (US); Vasu Rangadass, Arlington, TX (US); Ravi Seshadri, Plano, TX (US)

(73) Assignee: NANTHEALTH, INC., Culver City, CA (US)

( * ) Notice: Subject to any disclaimer, the term of this patent is extended or adjusted under 35 U.S.C. 154(b) by 671 days.

(21) Appl. No.: 14/657,679

(22) Filed: Mar. 13, 2015

(65) Prior Publication Data

US 2015/0269321 A1 Sep. 24, 2015

Related U.S. Application Data

(60) Provisional application No. 61/954,969, filed on Mar. 18, 2014.

(51) Int. Cl.
*G16H 50/00* (2018.01)
*G16H 50/20* (2018.01)
(Continued)

(52) U.S. Cl.
CPC ............ *G16H 50/20* (2018.01); *G06F 19/00* (2013.01); *G16H 50/30* (2018.01)

(58) Field of Classification Search
CPC ... G06F 19/345; G06F 19/3431; G16H 50/20; G16H 50/30; G16H 50/70
(Continued)

(56) References Cited

U.S. PATENT DOCUMENTS 8,463,595 B1 * 6/2013 Rehling ............ G06F 17/30864
704/9
2006/0229822 A1 * 10/2006 Theobald ............... G06Q 50/24
702/19
(Continued)

FOREIGN PATENT DOCUMENTS

EP 2541450 1/2013
WO WO 2015/142946 9/2015

OTHER PUBLICATIONS

Patrick, Kevin et al., "Health and the Mobile Phone," Am J. Prev Med 2008; 35(2), Elsevier, Inc., 2008 (pp. 177-181).
(Continued)

*Primary Examiner* — Hiep V Nguyen
(74) *Attorney, Agent, or Firm* — Stetina Brunda Garred and Brucker

(57) ABSTRACT

A method for facilitating a personal health operating system (PHOS) is provided in one example embodiment and includes extracting data into a mobile device that includes a portable health virtual machine executing the PHOS using a processor couples to a memory element, generating an N-gram dataset comprising data indicative and predictive of fitness of an individual, generating, in the PHOS, an N-gram from the N-gram dataset from the data according to a data structure indicative and predictive of fitness of an individual, the fitness including a numerical index representing a composite effect of various health conditions of the individual including interdependencies of the health conditions, generating an N-gram based on the N-gram dataset and calculating the individual's fitness using the N-gram.

24 Claims, 9 Drawing Sheets

(51) Int. Cl.
    *G16H 50/30* (2018.01)
    *G06F 19/00* (2018.01)
(58) Field of Classification Search
    USPC .......................................................... 705/3
    See application file for complete search history.

(56) References Cited

U.S. PATENT DOCUMENTS

| | | | |
|---|---|---|---|
| 2008/0162352 A1 | 7/2008 | Gizewski | |
| 2008/0288292 A1 | 11/2008 | Bi et al. | |
| 2010/0299135 A1* | 11/2010 | Fritsch | G06F 17/2785 704/9 |
| 2011/0082711 A1 | 4/2011 | Poeze et al. | |
| 2012/0089413 A1 | 4/2012 | Balassanian | |

OTHER PUBLICATIONS

Yip, Vincent, et al., "Concept Discovery for Pathology Reports using an N-gram Model", University of Arkansas for Medical Sciences Texas A&M University—Commerce, University of Central Arkansas, Mar. 1, 2010.
Wu, Cathy et al., "Back-Propagation and Counter-Propagation Neural Networks for Phylogenic Classification of Ribosomal RNA Sequences," Department of Epidemiology/Biomathematics, The University of Texas Health Center, Tyler, TX, Nucleic Acids Research, 1994, vol. 22, No. 20, 4291-4299 (9 pages).
Tandon, Nicket et al., "Information Extraction from Web-Scale N-Gram Data," Web N-Gram Workshop, SIGIR 2010 (8 pages).
Nadesan, Bala Sundra Ganapthy et al., "Improved N-gram Extraction and Substring Removal Algorithms with Efficient Dual-Pivot Sorting in Mining Data for UML Models," International Journal of Advanced Research in Computer Sciences and Software Engineering, vol. 33, Issue 7, Jul. 2013 (5 pages).
Osmanbeyoglu, Hatice Ulku et al., "N-gram Analysis of 970 Microbial Organisms Reveals Presence of Biological Language Models," BMC Bioinformatics, 2011 (12 pages).
Huang, Yu-Chen et al., "Using N-Gram Analysis to Cluster Heartbeat Signals," BMC Medical Informatics & Decision Making, 2012 (9 pages).
Wu, Cathy et al., "Protein Classification Artificial Neural System," Protein Science, 1, 667-677, 1992. (11 pages).
Zhang, Rui, "Automated Identification of Relevant New Information in Clinical Narrative," IHI,' 12, Jan. 28-30, 2012 (5 pages).
PCT International Search Report and Written Opinion in PCT International Application Serial No. PCT/US2015/021094 dated Jun. 18, 2015.
Article 19 Amendments filed in PCT International Application Serial No. PCT/US2015/021094 filed on Aug. 17, 2015.

* cited by examiner

PERSONAL HEALTH OPERATING SYSTEM

CROSS-REFERENCE TO RELATED APPLICATION

This application claims the benefit of priority under 35 U.S.C. § 119(e) to U.S. Provisional Patent Application Ser. No. 61/954,969, filed on Mar. 18, 2014 and entitled PERSONAL HEALTH OPERATING SYSTEM, the disclosure of which is hereby incorporated by reference in its entirety.

TECHNICAL FIELD

This disclosure relates in general to the field of healthcare systems and, more particularly, to a personal health operating system.

BACKGROUND

"mHealth" is a technology area that broadly encompasses use of mobile telecommunication and multimedia technologies in health care delivery. mHealth has emerged as a sub-segment of eHealth, with use of information and communication technology (ICT), such as computers, mobile phones, communications satellites, patient monitors, etc., for health services and information. mHealth applications typically include use of mobile devices in collecting community and clinical health data, delivery of healthcare information to practitioners, researchers, and patients, real-time monitoring of patient vital signs, and direct provision of care (via mobile telemedicine). mHealth operates on the premise that technology integration within the health sector has great potential to promote better health communication to achieve healthy lifestyles, improve decision-making by health professionals and patients, and enhance healthcare quality (e.g., by improving access to medical and health information and facilitating instantaneous communication through mobile technology). Moreover, increased use of mobile technology can reduce health care costs (e.g., by improving efficiencies in the health care system and promoting prevention through behavior change communication), and advance clinical care and public health services through better communication.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Overview

A personal health operating system (PHOS) is provided in one example embodiment and includes extracting data into a mobile device that includes a portable health virtual machine executing the PHOS using a processor couples to a memory element, generating an N-gram dataset comprising data indicative and predictive of fitness of an individual (e.g., user of the mobile device), generating, in the PHOS, an N-gram from the N-gram dataset from the data according to a data structure indicative and predictive of fitness of an individual, the fitness including a numerical index representing a composite effect of various health conditions of the individual including interdependencies of the health conditions, generating an N-gram based on the N-gram dataset and calculating the individual's fitness using the N-gram.

As used herein, the term "N-gram" refers to a sequence (e.g., contiguous or non-contiguous) of N primitives (grams) from a given collection of data (e.g., N-gram dataset) and representing a particular health condition combined with state information (e.g., progression index for comorbid conditions). The N-gram, which may be considered metaphorically similar to a gene sequence, can comprise one or more significant health related events that affect the individual's overall health. Note that a health related event comprises an interaction between the individual and externalities (e.g., objects, people and experiences external to the individual) in a manner that impacts any health condition of the individual. Each separate health condition may be represented by a corresponding separate N-gram. For example, a diabetes health condition may be represented by a sequence of diagnosis event, test event, etc. that together comprise the N-gram for the diabetes health condition.

EXAMPLE EMBODIMENTS

Figure 1:
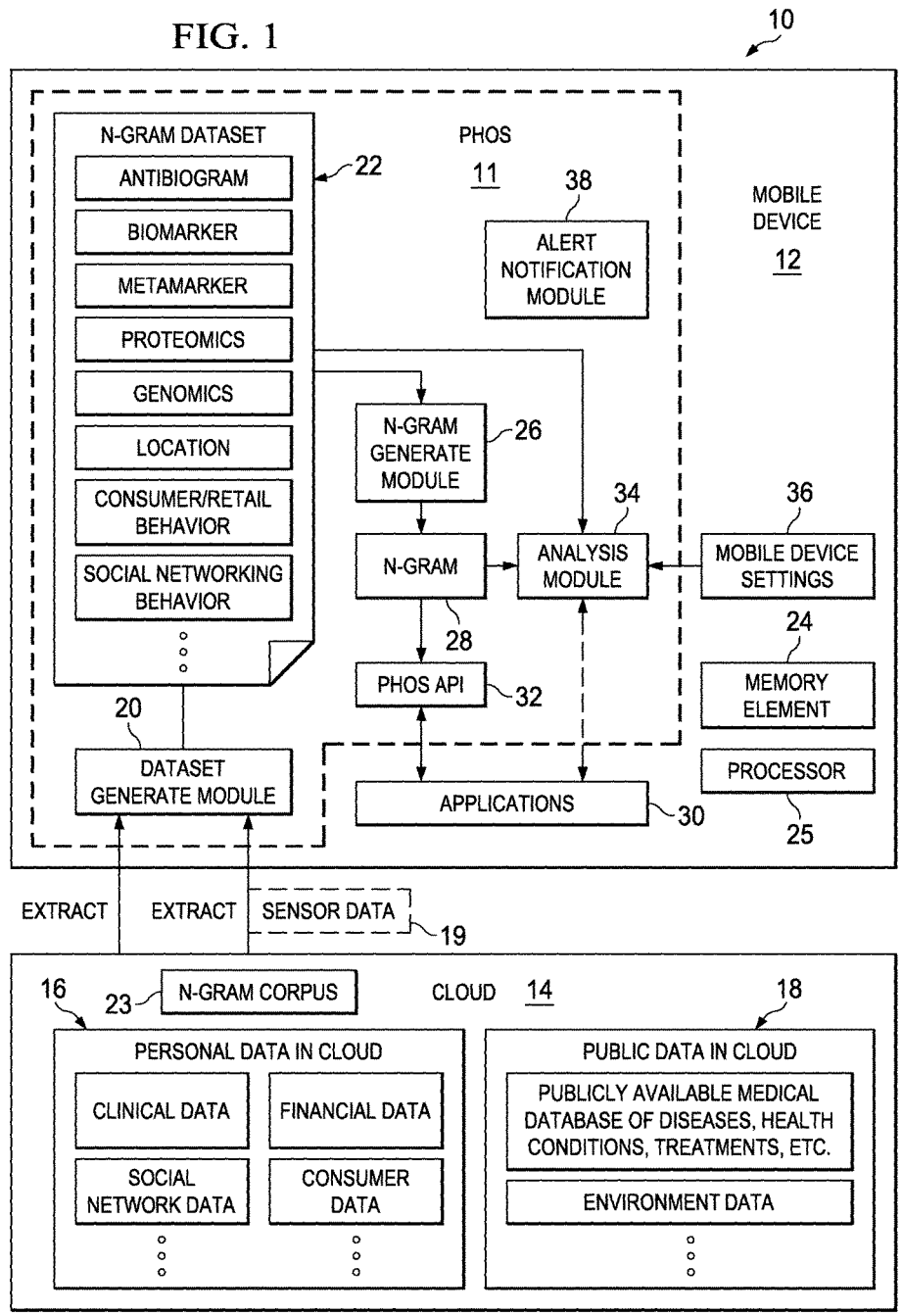
FIG. 1 is a simplified block diagram illustrating a system according to an example embodiment.

Turning to FIG. 1, FIG. 1 is a simplified block diagram illustrating a system 10 according to an example embodiment. System 10 may include a mobile device 12 executing a personal health operating system (PHOS) 11. Mobile device 12 includes any hardware wireless communication device that is capable of exchanging information in a wireless or cellular network environment, and can include, by way of examples and not as limitations, mobile phones, smart mobile phones, tablets, phablets, portable navigation systems, vehicles equipped with wireless communication, and multimedia devices.

Data in a cloud 14, including personal data 16 and public data 18, and sensor data 19 may be extracted (e.g., mined, retrieved, recovered, received, etc.) by a dataset generate module 20 in mobile device 12 to generate (e.g., derive, produce, create, develop, etc.) an N-gram dataset 22 from personal data 16 and public data 18, sensor data 19, and data from an N-gram corpus 23 in cloud 14 according to a data structure indicative and predictive of fitness of an individual (e.g., user of mobile device 12). Note that N-gram dataset 22 comprises a collection of separate data elements related by virtue of their association with the individual and which can be manipulated as a unit by PHOS 11. N-gram dataset 22 may correspond to a database, table, array, matrix, etc. based on particular needs.

As used herein, "fitness" comprises a numerical index (e.g., score, value, rate, scalar, vector, etc.) representing a composite effect of various health conditions of the individual, including their interdependencies. Note that health conditions includes illnesses, injuries, impairments, and physical or mental conditions that affect the health and well-being of the individual. Some health conditions may be minor and acute, such a temporary headache from a hangover; other health conditions may be major and chronic, such as coronary heart disease. Some health conditions may have no discernable effects until an event triggers reactions, such as bee sting allergy; other health conditions may have continuous effects, such as rheumatoid arthritis with long term deleterious effects on bone joints.

The fitness can indicate and/or predict health, wellbeing, vigor, stamina, strength, health condition, etc. of the individual based on the individual's health conditions and their interdependencies. For example, a person with optimal health may have blood pressure readings, blood sugar readings, pulse rate, blood alcohol level, etc. in a healthy range, resulting in high fitness; whereas a drunk consumer at a bar may have high blood alcohol level, resulting in low fitness. In another example, a person with diabetes only may have a certain fitness, whereas another person with both diabetes and hypertension may have a different fitness due to interdependencies of diabetes and hypertension. In yet another example, a person taking medication for epilepsy may experience a progressive degrading liver condition due to side effects of the medication and the person's physiology, and the fitness may comprehend such dependencies.

In various embodiments, an optimum fitness based on various disparate data values may be preconfigured in PHOS 11 for the individual. Different individuals may have different preconfigured optimum fitness based on personal medical history, or demographic information (e.g., age, gender, etc.), or other suitable parameters. In some embodiments, N-gram corpus 23 may include fitness indicative data pertaining to a population (e.g., group, plurality, etc.) of individuals; the data therein may be used to calculate the optimum fitness for the individual based on the individual's personal characteristics in relation to the population data.

Merely as examples, and not as limitations, data in N-gram dataset 22 can include anti-bio grams (e.g., result of a laboratory testing for sensitivity of an isolated bacterial strain to different antibiotics), biomarkers (e.g., measured characteristic used in the examination of normal biological processes, pathogenic processes, or pharmacologic responses to a therapeutic intervention), meta-markers (e.g., markers of a marker; for example, fever is a marker of cytokines, which itself is a marker of hypotension due to septicemia), proteomics (e.g., study of proteins), genomics (e.g., study of genomes), location, consumer/retail behavior (e.g., credit card charges, shopping sites, etc.), and social networking behavior (e.g., contacts, personal information, etc.). Virtually any data that can be used to indicate fitness and/or predict fitness may be included in N-gram dataset 22 within the broad scope of the embodiments.

In various embodiments, such data may be readily available through cloud 14 without further analysis; in other embodiments, such data may be determined from analysis of available information in cloud 14. For example, an individual's social network may be analyzed to identify related family members; information from social media interactions with such family members may be analyzed to determine or augment a family history of health conditions; such information may be added to genomics data in N-gram dataset 22; etc. Any suitable method to create N-gram dataset 22 may be included within the broad scope of the embodiments.

Virtually any suitable data that can be accessed through cloud 14 and from sensors may be used to generate N-gram dataset 22 are included within the broad scope of the embodiments. In a general sense, data, including personal data 16, public data 18, and sensor data 19 refers to any type or modality of numeric, text, voice, video, or script data, or any type of source or object code, or any other suitable information in any appropriate format that may be communicated from one point to another in electronic devices and/or networks. Note that sensors generating sensor data 19 may be connected to mobile device 12 through appropriate communication channels (e.g., embedded, wired, or wireless (e.g., near field communication, Bluetooth, etc.) suitably sufficient to allow dataset generate module 20 to access and obtain the data therefrom.

For example, personal data 16 can include clinical data, financial data, social network data, consumer data, etc. which can be used to generate N-gram dataset 22. For example, clinical data can include information (e.g., facts) related to diagnosis and treatment of a current or potential health condition (e.g., disease, diabetes, obesity, aging, etc.), demographic information (e.g., age, weight, gender) that may be relevant to diagnosis and treatment of a current or potential health condition, data generated during clinical encounters (e.g., visit at physician's office, clinics, hospitals, laboratory testing, in-home testing), data generated from medical sensors and equipment, etc. Financial data can include bank statements, credit card charges, stock trades, etc. Social network data can include social networking sites, data input by the individual or his/her contacts, etc. Consumer data can include shopping sites, visited shops, retail memberships, shopping preferences, purchased goods, eating and drinking outlets like restaurants and bars and sports and recreation areas parks, fitness facilities, tennis courts), etc. In another example, public data 18 can include any publicly available medical database of diseases, health conditions, treatments, etc., environment data (e.g., weather, terrain, etc.), news, etc.

Substantially all personal data 16 may be extracted upon receiving consent to do so from the relevant individual/owner of personal data 16. In some embodiments, dataset generate module 20 may ask for user permission to extract (e.g., download) a specific data at a time of extraction, possibly within a homomorphic encryption environment. In other embodiments, dataset generate module 20 may ask for user permission to extract substantially all accessible personal data 16 during installation of PHOS 11. In yet other embodiments, the individual may implicitly provide permission by giving access to personal data 16 in cloud 14 (e.g., through appropriate user names, passwords, security certificates, etc.).

A memory element 24 and a processor 25 may be used to execute the operations of system 10. PHOS 11 may also include an N-gram generate module 26 that can generate an N-gram 28 from N-gram dataset 22. N-gram 28 may be exposed to applications 30 through a PHOS application programming interface (API) 32. An analysis module 34 may analyze N-gram dataset 22 and N-gram 28, according to mobile device settings 36 (and applications 30, as needed and based upon particular specifications/configurations).

An alert notification module 38 may be configured to alert the individual when predictions and/or analysis results based on N-gram 28 indicate a fitness change exceeding a preconfigured (e.g., predetermined) threshold. In an example embodiment, the threshold may be set around an optimum fitness of the individual, for example, as a range (e.g., optimum fitness ±2σ, where σ is the standard deviation of the data). Any deviation from the optimum fitness by more than the threshold can result in an alert. In another example embodiment, the threshold may range around trends in the fitness. For example, a decreasing fitness trend larger than a preconfigured threshold rate may result in an alert. In some embodiments, the alert can be positive in nature (e.g., indicating that the individual is "doing a good job"); in other embodiments, the alert can be negative in nature (e.g., indicating "don't do that"). Any suitable form of alert (e.g., text, pop up window, beeps and other sounds, etc.) may be used within the broad scope of the embodiments.

According to various embodiments, dataset generate module 20 may format data in N-gram dataset 22 according to a particular data structure, such as: [coded-longitudinal-time].[coded-condition-category].[coded-phenotype-data].[coded-evidence-index].[condition-aggrevation-index]. The data structure may serve to provide a virtual view of N-gram 28 with an anchor for a given dominant (e.g., requested) clinical condition (e.g., health condition, disease, etc.).

In various embodiments, the data structure for N-gram dataset 22 can overcome existing limitations for representations of constituents versus dependency, where existing representations use a "data mart" approach to create a "constituent model" thereby repeating information redundantly without elegantly representing the impact of inter-dependency of a single health related event to multiple conditions. In various embodiments, the data structure may be formatted to capture the essence of a health related event in a coded form over longitudinal time. For example, N-gram 28 generated for the health related event can capture significant aspects of the health related event based on the coded N-gram dataset 22.

Note that examples of health related events include diagnosis events (e.g., where diagnosis of a medical condition is made), testing events (e.g., where a biological parameter of the individual is tested), imaging events (e.g., where various kinds of health care related images of the individual are taken), eating events (e.g., where the individual imbibes food and drinks that affect the individual's health conditions), social events (e.g., where the individual is in a social setting that can affect health conditions), or any other events that affect the health condition of the individual (including the user of mobile device 12).

In some embodiments, some parameters in N-gram dataset 22 may not occur frequently relative to other parameters. For example, for a person with high blood pressure, but normal blood sugar, parameters indicative of the high blood pressure condition, including blood pressure readings, blood pressure medications, stroke events, etc., may occur more frequently than blood sugar readings, diabetes events or hypoglycemia events. Consequently, the resolving power of the predictor based on the low frequency parameters may have low statistical confidence. Low statistically confidence can be overcome in some embodiments by augmenting the statistics with N-gram 28 from similar individuals having similar attributes (e.g., age, gender, health state, geo-location, etc.), for example, gleaned from N-gram corpus 23.

Turning to the data structure of data in N-gram dataset 22, assume, merely as an example and not as a limitation, that data in N-gram dataset 22 includes timestamps coded as universal time code (UTC); location coded as a combination of latitude and longitude; various health conditions coded appropriately (e.g., cardiovascular condition coded as CARDIO, diabetic condition coded as ENDOCR, etc.); phenotype data coded appropriately (e.g., hypertension coded as HT with corresponding value of none, low, or high; diabetics coded as DB with corresponding value of none, low, or high, etc.); evidence data coded according to fields (e.g., BPDATA field with corresponding blood pressure value, A1CDATA field with corresponding A1C blood test values); etc. In some embodiments, N-gram generate module 26 may parse through N-gram dataset 22 according to a filter represented by N-gram 28 and extract appropriate coded data therein to feed into analysis module 34.

In an example, a diagnosis event of "hypertension" may be represented by N-GRAM 28 as follows: UTC.LAT:LONG.CARDIO.HT:HIGH.[BPDATA].NIH:HT01.[Computed Aggravation Index based on personal+family+social history], where HT: HIGH represents a coded phenotype data for hypertension with a value of "high"; [BPDATA] represents a coded evidence index, indicating blood pressure data and corresponding value; NIH:HT01 represents a uniform code for hypertension, stage 1; and [Computed Aggravation Index based on personal+family+social history] represents a computed aggravation index indicating the extent of aggravation from contributing factors such as personal history, family history and social history (e.g., a smoker may aggravate his medical condition due to his personal history of smoking and the smoker's aggravation index from personal history may be higher than a non-smoker's corresponding aggravation index).

In another example, a diagnosis event of "diabetes" may be represented by N-gram 28 as follows: UTC.LAT:LONG.ENDOCR.DB:HIGH.A1CDATA.NIH:DB01.[Computed Aggravation Index based on personal+family+social history], where UTC represents a coded-longitudinal time; LAT: LONG represents a coded location category; ENDOCR represents the condition category for endocrine health; DB: HIGH represents a coded phenotype data for diabetes, with a value of "high"; [A1CDATA] represents a coded evidence index, indicating A1C data and corresponding value; NIH:DB01 represents a uniform code for diabetes, stage 1; and [Computed Aggravation Index based on personal+family+social history] represents the computed aggravation index indicating the extent of aggravation from contributing factors such as personal history, family history and social history.

For a person with both hypertension and diabetes, the aggravation index on occurrence of the second event in time may be computed based on both health conditions (e.g., aggravation index may be higher for a patient with both conditions than for another patient with only one of the conditions). In some embodiments, a comorbidity corpus can be used to track a comorbid, holistic or dominant condition trajectory and to compute the aggravation index.

In some embodiments, for a repeat of a health related event, N-gram 28 may capture an optimistic concurrency control (OCC) of the time and location, for example, as UTC.LAT:LONG.ENDOCR.DB:HIGH.[A1CDATA]NIH:DB01.[Computed Aggravation Index based on personal+family+social history]:[OCC:[TimeStamp:Lat:Long]]. Thus, transactions representing health related events that repeat in different time or locations may be identified as such through OCC algorithms. Note that any suitable OCC algorithm may be implemented in PHOS 11 within the broad scope of the embodiments.

In a general sense, N-gram 28 can be used for efficient approximate matching. For example, by converting a sequence of data to N-gram 28, the data can be embedded in a vector space, thus allowing the sequence to be compared to other sequences in an efficient manner. Vectors can create efficiencies for matching (e.g., tree structures) or for distance comparison (e.g., Euclidean distance, Hamming distance, etc.) In a general sense, vectors represented by N-gram 28 may exist in well-defined namespace.

Example applications of N-gram 28 include statistical language modeling (e.g., for textual mapping and comparisons to determine associations and classifications, extracting concepts from medical reports and narratives, phrase and topic discovery), database searching (e.g., searching molecular databases for genomic and proteomic sequences), sequence generation (e.g., for heartbeat analysis, genomic classification) etc. In general, many indexing, retrieval, and comparison methods can be based on counting or cataloguing N-gram 28 in streams of symbols.

In the various embodiments, N-gram 28 can be indicative and predictive of fitness of the individual to whom N-gram dataset 22 pertains. In some embodiments, different N-grams 28 may be generated for different aspects of fitness. For example, N-gram A may be indicative of diabetics conditions of the individual; N-gram B may be indicative of heart conditions of the individual; N-gram C may be indicative of the individual's stamina; N-gram D may be indicative of the individual's medication interaction propensities and allergies; and so on. Virtually any number and type of N-gram 28 may be generated within the broad scope of the embodiments.

In some embodiments, N-gram generate module 26 may query sequences of n data points in N-gram dataset 22. Estimating the number of distinct N-grams can be a view-size estimation problem. In an example embodiment, N-gram generate module 26 may implement a one-pass one-hash algorithm for accurate estimates of the number of distinct N-grams when the hashing is sufficiently independent (e.g., no two N-grams are hashed to the same value). In an example embodiment, the N-gram hashing function extracts and counts occurrences of patterns of n consecutive items (e.g., sliding window of size n) from a sequence string. For example, term frequency-inverse document frequency (tf-idf) (e.g., a numerical statistic that reflects how important a word is to a corpus) may be used to determine frequency of specific patterns in N-gram dataset 22. Any suitable N-gram extraction method may be implemented by N-gram generate module 26 to generate N-gram 28 within the broad scope of the embodiments.

To count the N-grams, a given pattern $p \in P$ can be instantiated for specific candidate tuples (x;y) as p(x;y) to yield an N-gram string. For instance, a pattern such as "<X>: <Y>" can be instantiated with a tuple <glucose level, 105> to yield an N-gram A "glucose level: 105". N-gram dataset 22 may be consulted to obtain raw or manipulated frequency information f(p(x;y)) that reveals how frequently N-gram A occurs in the data. In some embodiments, N-gram generate module 26 takes a string (e.g., data in N-gram dataset 22) as input, breaks it into a list of units ("tokens"), and finds each successive group of n consecutive or non-consecutive tokens in N-gram dataset 22.

In some embodiments, the data in N-gram dataset 22 may be reviewed and portions of the data may be assigned tokens representing health related events associated with the respective portions. In some embodiments, N-gram 28 may be generated according to a desired (e.g., requested) ordering. For example, time ordering may be used for longitudinal analysis. Other orderings (e.g., location orderings) may also be applied based on particular needs. In some embodiments, token T1 in N-gram 28 may generate many possible candidates of data C(T1). The candidates C(T1) can be ranked by frequency in N-gram dataset 22, severity, and/or other parameters of interest. The fitness of the individual can be calculated as a function of possible candidates C(T1) (e.g., fitness=$\Sigma a_j T_j$, $T_j \in C(T1)$; etc.)

In various embodiments, a plurality of N-gram 28 may be generated and N-gram dataset 22 analyzed accordingly, with each N-gram 28 predictive (or indicative) of a different health condition. A plurality of N-gram strings may be used substantially simultaneously to analyze data in N-gram dataset 22. In some embodiments, a set of predicated N-grams can provide a leading indicator of possible events. For example, analysis of N-gram dataset 22 using N-gram A can indicate that N-gram B, a predicate of N-gram A, indicates heart attack for the individual.

In a general sense, N-gram 28 may be useful in predictions with historical information scaled based on "N" (e.g., number of grams in N-gram 28). In some embodiments, the prediction may be based on a 1-gram analysis, 2-gram analysis, 3-gram analysis and so on. The statistical confidence of predication can be measured consistency of the analyses (e.g., if predication is nearly the same for N analyses, then confidence is high).

In some embodiments, a set of possible health related events that could take place in a particular situation may be defined in an event vocabulary by dataset generate module 20 in N-gram dataset 22. The vocabulary may comprise, by way of examples and not as limitations, "heart attack," "stroke," "hypothermia," "anaphylaxis," "hypoglycemia," "blood alcohol level," etc. Each gram in the vocabulary could be a scalar or unitary value (e.g., "heart attack, broken leg, GUID, etc.) in some embodiments. In other embodiments, each gram could have multiple values. For example, the health condition name and severity (hypertension: high) may comprise a single gram facilitating measuring N-gram 28 by name and significance or severity or value or equivalent. Each gram, N of which comprise an N-gram, may be normalized so that system 10 operates in the same namespace irrespective of the gram type. In some embodiments, each gram may comprise an attribute-value pair (e.g., {vigor::34}).

In various embodiments, N-gram 28 can built up statistical models of health related events based on populations. For example, a statistical model based on gender may utilize a particular N-gram 28; another statistical model based on age may utilize another N-gram 28; yet another statistical model based on location may utilize yet another N-gram 28; yet another statistical model based on genomic attributes may utilize yet another N-gram 28; and so on. Moreover, N-gram 28 generated in mobile device 12 may pertain to a specific individual (e.g., personalized N-gram), whereas other N-grams generated based on N-gram corpus 23 in cloud 14 may comprise a cohort N-gram with respect to groups of people.

Turning to the infrastructure of system 10, mobile device 12 may operate in various wireless communication networks such as Code division multiple access (CDMA), Time division multiple access (TDMA), Frequency Division Multiple Access (FDMA), Orthogonal Frequency-Division Multiple Access (OFDMA), Single Carrier Frequency-Division Multiple Access (SC-FDMA) and other networks. A CDMA network may implement a radio technology, such as UTRA, Telecommunications Industry Association's (TIA's) CDMA2000®, and the like. The UTRA technology includes Wideband CDMA (WCDMA) and other variants of CDMA. The CDMA2000® technology includes the IS-2000, IS-95 and IS-856 standards from the Electronics Industry Alliance (EIA) and TIA.

The TDMA network may implement a radio technology, such as Global System for Mobile Communications (GSM). An OFDMA network may implement a radio technology, such as Evolved UTRA (E-UTRA), Ultra Mobile Broadband (UMB), IEEE 802.11 (Wi-Fi), IEEE 802.16 (WiMAX), WiGIG 802.11ad, IEEE 802.20, Flash-OFDMA, and the like. The UTRA and E-UTRA technologies are part of Universal Mobile Telecommunication System (UMTS). 3GPP Long Term Evolution (LTE) and LTE-Advanced (LTE-A) are newer releases of the UMTS that use E-UTRA. UTRA, E-UTRA, UMTS, LTE, LTE-A and GSM are described in 3GPP documents. CDMA2000® and UMB are described in 3GPP2 documents. The techniques described herein may be used for the wireless networks and radio access technologies mentioned above, as well as other wireless networks and radio access technologies. Mobile device 12 may also communicate using near field communication (NFC), Bluetooth, RFID, Wi-Fi, or other wireless technologies (e.g., IEEE 802.11x).

Mobile device 12 may also implement other mobile operating systems that can combine features of a personal computer operating system with other features, including a touchscreen, cellular, Bluetooth, Wi-Fi, GPS mobile navigation, camera, video camera, speech recognition, voice recorder, music player, near field communication, etc. In a general sense, the mobile operating system includes a user-facing software platform supplemented by a second low-level real-time operating system that operates the radio and other hardware.

Data exchanges among mobile device 12 and cloud 14 and sensors and other devices can also be conducted over a packet-switched network, the Internet, LAN, WAN, VPN, or other type of packet switched network; a circuit switched network; cell switched network; or other type of network. Elements of FIG. 1 may be coupled to one another through one or more interfaces employing any suitable connection (wired or wireless), which provides a viable pathway for electronic communications. Additionally, any one or more of these elements may be combined or removed from the architecture based on particular configuration needs.

The network in which mobile device 12 communicates offers a communicative interface between various network components, and may include any local area network (LAN), wireless local area network (WLAN), metropolitan area network (MAN), Intranet, Internet, Extranet, wide area network (WAN), virtual private network (VPN), or any other appropriate architecture or system that facilitates communications in a network environment. The network may implement any suitable communication protocol for transmitting and receiving data packets within system 10. The architecture of the present disclosure may include a configuration capable of TCP/IP, TDMA, and/or other communications for the electronic transmission or reception information in a network. The architecture of the present disclosure may also operate in conjunction with any suitable protocol, where appropriate and based on particular needs. In addition, gateways, routers, switches, and any other suitable nodes (physical or virtual) may be used to facilitate electronic communication between various nodes in the network.

Note that the numerical and letter designations assigned to the elements of FIG. 1 do not connote any type of hierarchy; the designations are arbitrary and have been used for purposes of teaching only. Such designations should not be construed in any way to limit their capabilities, functionalities, or applications in the potential environments that may benefit from the features of system 10. It should be understood that system 10 shown in FIG. 1 is simplified for ease of illustration.

In various embodiments, PHOS 11 is configured to interface with the mobile operating system of mobile device 12 to enable appropriate use of memory element 24, processor 25 and various mobile device settings 36, among other functions. Mobile device 12 also includes a suitable user interface, including a touchscreen, data interface, web interface, authentication portal, and other objects and modules to facilitate the operations described herein. In various embodiments, PHOS 11 may comprise a firmware executing on mobile device 12 with access permissions to operate the hardware and software. In other embodiments, PHOS 11 may comprise a collection of software executing on mobile device 12 with access permissions to operate the hardware and software as indicated by the individual (e.g., individual gives permission to PHOS 11 to use the sensors, data, etc. as needed) and that provides common services for applications 30. In some embodiments, PHOS 11 may include firmware (e.g., device drivers, kernels, etc.) and software executing in mobile device 12.

Cloud 14 is a collection of hardware and software forming a shared pool of configurable computing resources (e.g., networks, servers, storage, applications, services, etc.) that can be suitably provisioned to provide on-demand self-service, network access, resource pooling, elasticity and measured service, among other features. Cloud 14 may be deployed as a private cloud (e.g., infrastructure operated by a single enterprise/organization), community cloud (e.g., infrastructure shared by several organizations to support a specific community that has shared concerns), public cloud (e.g., infrastructure made available to the general public), or a suitable combination of two or more disparate types of clouds. In some embodiments, cloud 14 may be managed by a cloud service provider, who can provide subscribers (e.g., mobile device 12) with at least access to cloud 14, and authorization to use cloud resources in accordance with predetermined service level agreements.

Sensors generating sensor data 19 can include camera, GPS location sensor, health monitoring equipment, and any other device that can communicate with mobile device 12 (e.g., by embedded, wired or wireless means) and provide data suitable to be included in N-gram dataset 22. Other examples of sensors that generate sensor data 19 can include pulse-oximeter, micro-spirometer, thermometer, peroxide sensor, etc.

In some embodiments, applications 30 may be installed and may execute on mobile device 12. As used herein, the term "application" can be inclusive of an executable file comprising instructions that can be understood and processed on a computer, and may further include library modules loaded during execution, object files, system files, hardware logic, software logic, or any other executable modules. In other embodiments, applications 30 may be installed on a remote network device with access to mobile device 12 through a suitable network (e.g., wireless network). Note that virtually any number of applications 30 may be installed and may execute in mobile device 12 within the broad scope of the embodiments.

In some embodiments, analysis module 34 may be used to analyze N-gram 28, for example, over time, varying fitness parameters (e.g., stored in N-gram dataset 22), etc. Analysis module 34 can analyze fitness, for example, to illustrate effects of certain events (e.g., clinical interventions, diet, exercise, etc.) on fitness. In some embodiments, analysis module 34 can provide a snapshot of the individual's fitness at a certain instant of time; in other embodiments, analysis module 34 can provide a time-varying graph of the individual's fitness over a specified time period (e.g., month); in yet other embodiments, analysis module 34 can predict fitness in the future based on fitness in the present (or the past) based on individual behavior, and other parameters. Analysis module 34 can provide analysis of N-gram 28 to determine medication interactions, effect of certain dietary ingredients, safe dosages of alcohol, etc. Virtually any suitable analysis of N-gram 28 relevant to fitness and using data in N-gram dataset 22 may be performed by analysis module 34 within the broad scope of the embodiments.

In certain embodiments, analysis module 34 may be preconfigured with certain capabilities (e.g., analyze N-gram 28 over time, and for certain pre-determined events). Capabilities of analysis module 34 may be expanded by interactions with applications 30 through PHOS API 32 suitably. For example, applications 30 may cause analysis module 34 to analyze N-gram 28 for particular variations, data, trends, etc.

Note that the numerical and letter designations assigned to the elements of FIG. 1 do not connote any type of hierarchy; the designations are arbitrary and have been used for purposes of teaching only. Such designations should not be construed in any way to limit their capabilities, functionalities, or applications in the potential environments that may benefit from the features of system 10. It should be understood that the system 10 shown in FIG. 1 is simplified for ease of illustration.

Figure 2:
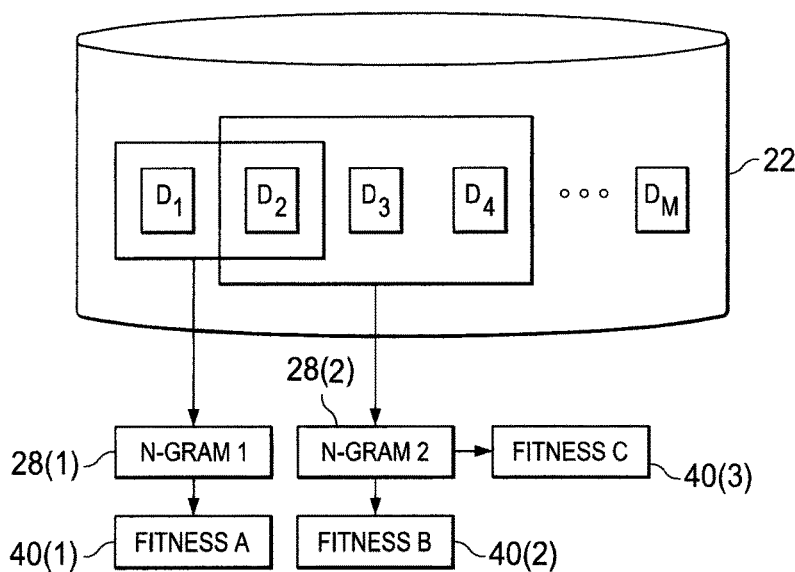
FIG. 2 is a simplified diagram illustrating example details of an embodiment of the system.

Turning to FIG. 2, FIG. 2 is a simplified diagram illustrating example details according to an embodiment of system 10. N-gram dataset 22 may comprise one or more data items $D_1 \ldots D_M$, which may be used to generate one or more N-grams 28(1), 28(2), which may, in turn, be used to indicate, derive, or predict fitness 40(1)-40(3). For example, N-gram 28(1) may be indicative of fitness A 40(1), which relates to the diabetics condition of the individual (by way of example, and not as a limitation). A change in N-gram 28(1) may indicate a change in corresponding fitness A 40(1). For example, N-gram 28(1) may specify "glucose level: 95;" N-gram 28(1) may change to "glucose level: 110" based on sensor data 19 after a glucose test using one or more sensors. Fitness A 40(1) derived from the changed N-gram 28(1) may indicate a change in diabetics condition. In another example, N-gram 28(2) may be indicative of two fitness characteristics, fitness B 40(2) and fitness C 40(3), which can represent, by way of example and not limitation, heart health and stamina. Virtually any suitable N-gram 28 may be generated from N-gram dataset 22; the generated N-gram 28 may be used to represent any number of corresponding fitness (e.g., 40(1)-40(3)).

In some embodiments, any updates to data in N-gram dataset 22 may trigger generation or modification of N-grams 28(1)-28(2). In other embodiments, N-grams 28(1)-28(2) may be generated or modified at predefined periodic intervals. In yet other embodiments, N-grams 28(1)-28(2) may be generated or modified at individual request. In yet other embodiments, N-grams 28(1)-28(2) may be generated or modified according to instructions from applications 30.

Figure 3:
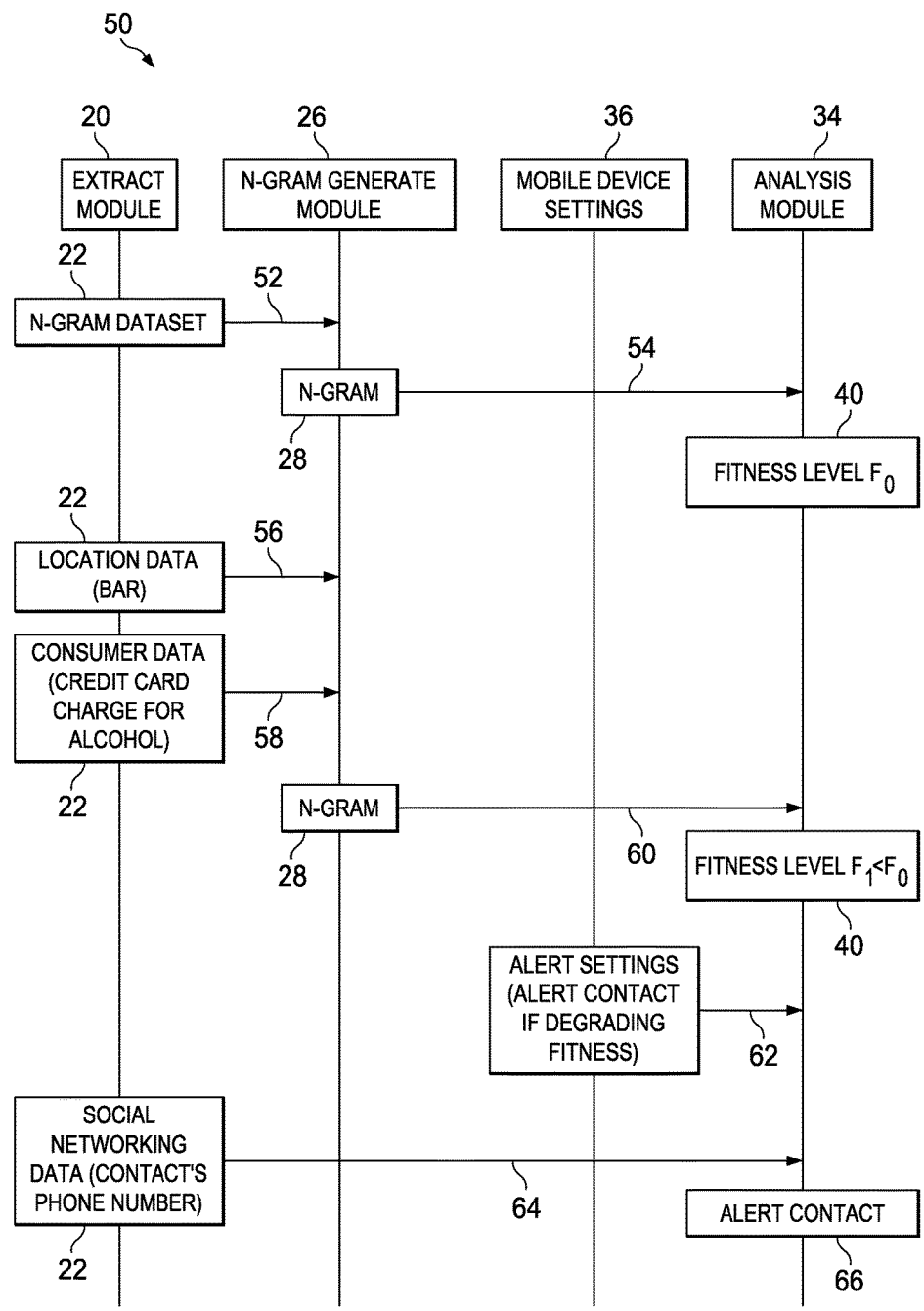
FIG. 3 is a simplified sequence diagram illustrating potential operations that may be associated with an embodiment of the system.

Turning to FIG. 3, FIG. 3 is a simplified sequence diagram illustrating example operations 50 that may be associated with embodiments of system 10. At 52, data from N-gram dataset 22 may be accessed by N-gram generate module 26 to generate N-gram 28. At 54, analysis module 34 may use N-gram 28 to derive fitness $F_0$ 40 at time $T_0$. At 56, updated location data (e.g., indicating a bar) may be extracted by dataset generate module 20, populated in N-gram dataset 22, and used by N-gram generate module 26. At 58, updated consumer data (e.g., indicating credit card charge for alcohol) may be extracted by dataset generate module 20, populated in N-gram dataset 22, and used by N-gram generate module 26 to generate N-gram 28.

At 60, analysis module 34 may use the updated N-gram 28 to derive fitness $F_1$ 40 at time $T_1$. Analysis module 34 may determine that $F_1$ is less than $F_0$, indicating a deteriorating fitness. At 62, mobile device settings 36 may be accessed to determine appropriate settings (e.g., preconfigured settings may indicate alerting a particular contact (e.g., spouse) if degrading fitness is sensed. At 64, analysis module 34 may access N-gram dataset 22 to retrieve social networking data (e.g., contact's phone number). At 66, analysis module 34 may generate and send an alert to the contact.

Figure 4:
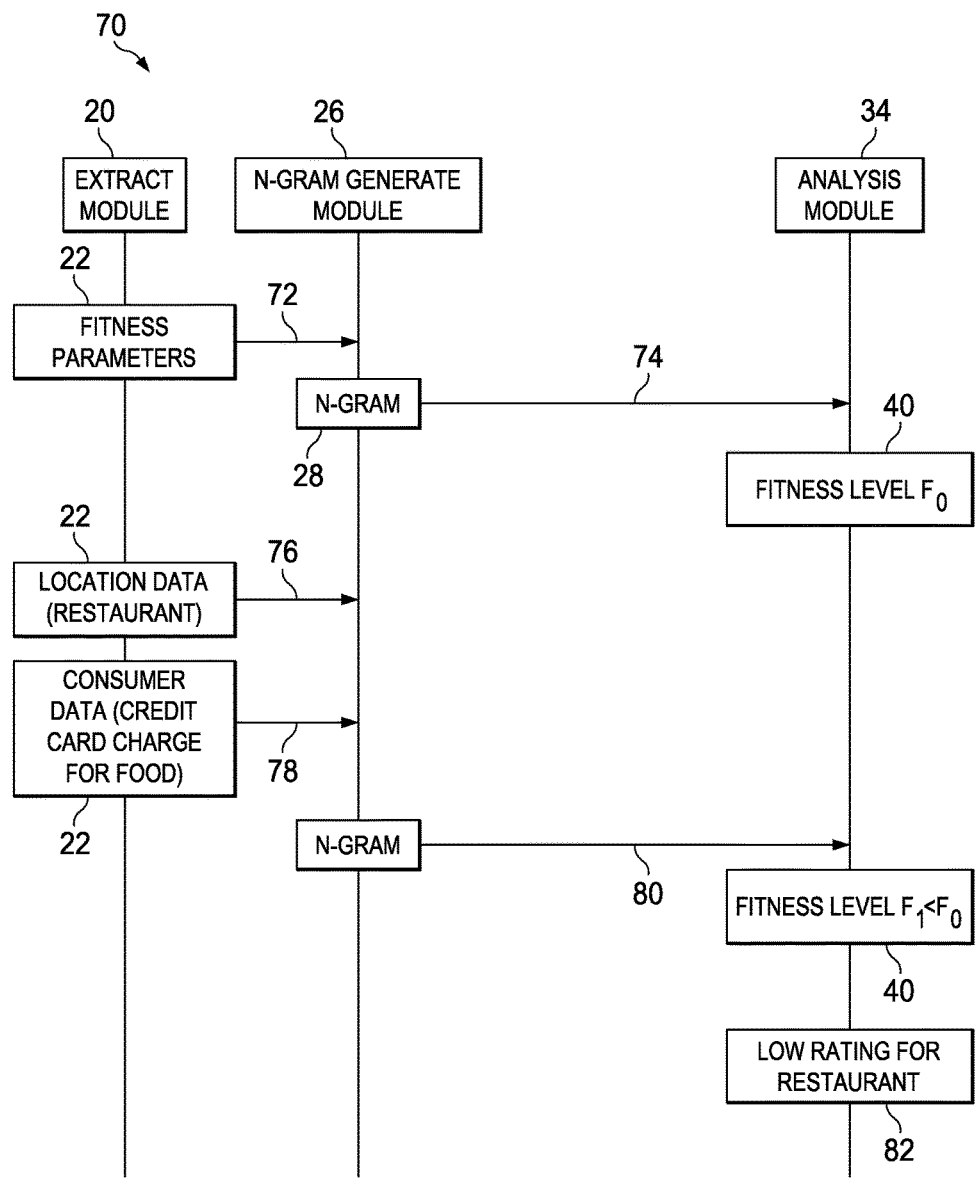
FIG. 4 is a simplified sequence diagram illustrating other potential operations that may be associated with an embodiment of the system.

Turning to FIG. 4, FIG. 4 is a simplified sequence diagram illustrating example operations 70 that may be associated with embodiments of system 10. At 72, data from N-gram dataset 22 may be accessed by N-gram generate module 26 to generate N-gram 28. At 74, analysis module 34 may use N-gram 28 to derive fitness $F_0$ 40 at time $T_0$. At 76, updated location data (e.g., indicating a restaurant) may be extracted by dataset generate module 20, populated in N-gram dataset 22, and used by N-gram generate module 26.

At 78, updated consumer data (e.g., indicating credit card charge for food) may be extracted by dataset generate module 20, populated in N-gram dataset 22, and used by N-gram generate module 26 to generate N-gram 28. At 80, analysis module 34 may use the updated N-gram 28 to derive fitness $F_1$ 40 at time $T_1$. Analysis module 34 may determine that $F_1$ is less than $F_0$, indicating a deteriorating fitness. The deteriorating fitness may be caused by eating the restaurant food. At 82, analysis module 34 may generate a low rating for the restaurant based on the deteriorated fitness.

Figure 5:
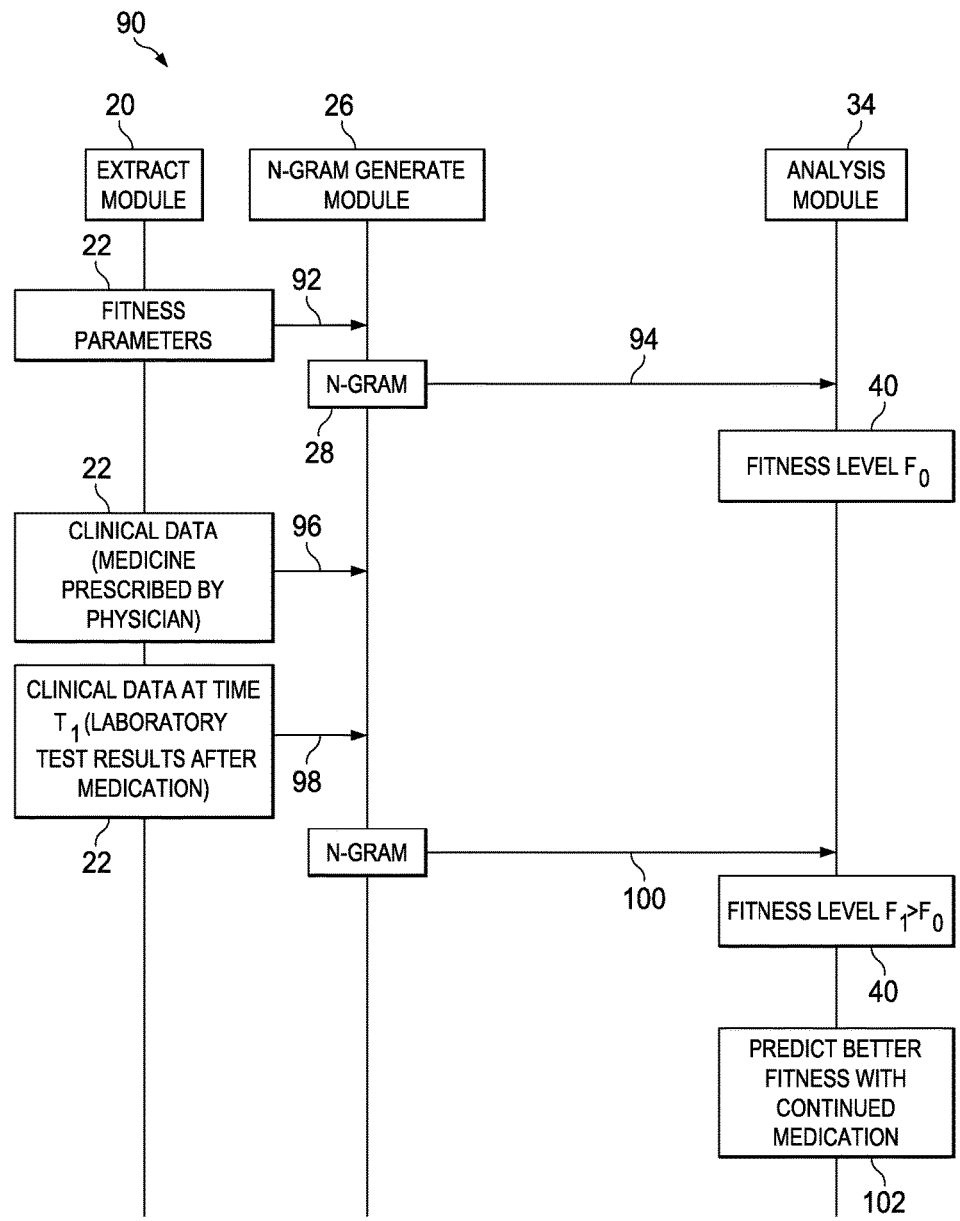
FIG. 5 is a simplified sequence diagram illustrating yet other potential operations that may be associated with an embodiment of the system.

Turning to FIG. 5, FIG. 5 is a simplified sequence diagram illustrating example operations 90 that may be associated with embodiments of system 10. At 92, data from N-gram dataset 22 may be accessed by N-gram generate module 26 to generate N-gram 28. At 94, analysis module 34 may use N-gram 28 to derive fitness $F_0$ 40 at time $T_0$. At 96, updated clinical data (e.g., indicating medication prescribed by physician) may be extracted by dataset generate module 20, populated in N-gram dataset 22, and used by N-gram generate module 26.

At 98, updated clinical data at time $T_1$ (e.g., indicating laboratory test results after medication) may be extracted by dataset generate module 20, populated in N-gram dataset 22, and used by N-gram generate module 26 to generate N-gram 28. At 100, analysis module 34 may use the updated N-gram 28 to derive fitness $F_1$ 40 at time $T_1$. Analysis module 34 may determine that $F_1$ is better than $F_0$, indicating increased fitness. At 102, analysis module 34 may predict better fitness with continued medication.

Figure 6:
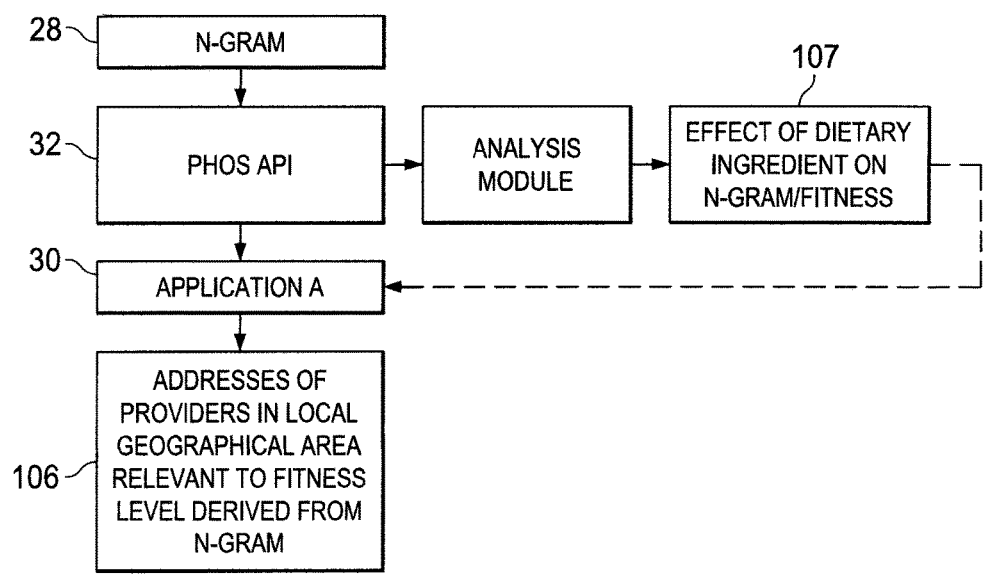
FIG. 6 is a simplified block diagram illustrating other example details of an embodiment of the system.

Turning to FIG. 6, FIG. 6 is a simplified block diagram illustrating example details of an embodiment of system 10. N-gram 28 may be exposed by PHOS API 32 to application 30. In various embodiments, PHOS API 32 may expose various APIs to applications 30. By way of examples and not as limitations, the APIs may include, "getNgram(*context), zeroNgram(NgramID), cmpNgram(Ngram1, Ngram2), deleteNgram(NgramID), addEventToCorpus(EventID), addNgramToCorpus( ) etc.

By way of example, and not as a limitation, a specific example application A 30 may be configured to generate addresses 106 of health care providers in a local geographic area relevant to fitness derived from N-gram 28. In another example, application 30 may interact with analysis module 34 through PHOS API 32, and instruct analysis module 34 to analyze effect 107 of a particular dietary ingredient on N-gram 28 and fitness of the individual. The results may be provided to application 30 for further analysis and use, based on the application capabilities. Virtually any appropriate, user-consented use of N-gram 28 and analysis module 34 may be facilitated by PHOS API 32 within the broad scope of the embodiments.

Figure 7:
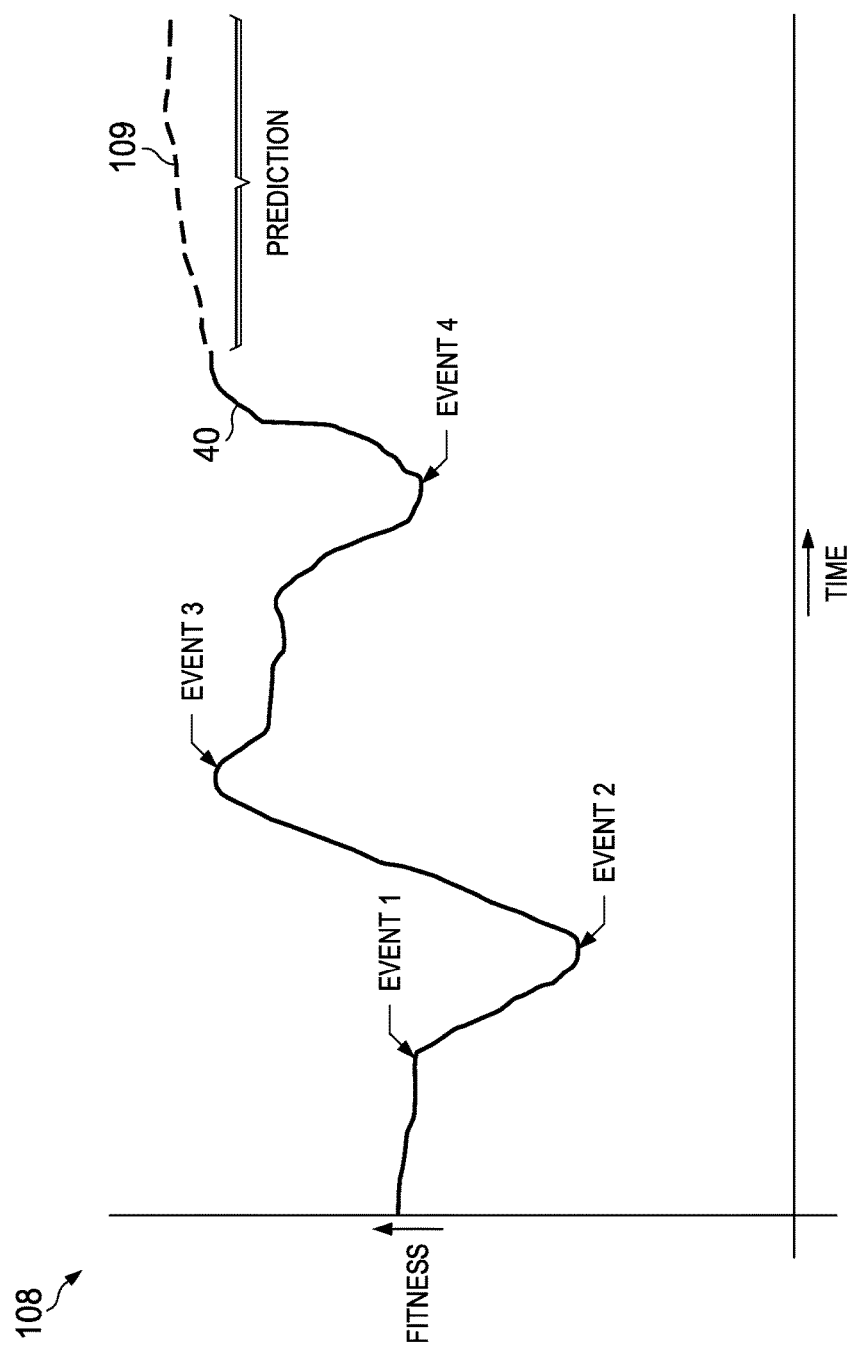
FIG. 7 is a simplified block diagram illustrating yet other example details of an embodiment of the system.

Turning to FIG. 7, FIG. 7 is a simplified diagram illustrating an example graph 108 of time varying fitness 40 according to an embodiment of system 10. In some embodiments, analysis module 34 may analyze N-gram 28 over time, and generate graph 108, which may be displayed to the individual on the mobile device touchscreen. In some embodiments, health related events (e.g., event 1, event 2, event 3, event 4, etc.) may be displayed or located on the graph to show its impact on fitness. Analysis module 34 may also provide a prediction 109 for a future time based on the present (and past) fitness and predicted individual behavior in the future time period. In some embodiments, the N-gram analysis can predict the next expected gram to occur in a sequence based on the statistical (e.g., frequency) of the sequence and subsequent (or preceding) gram in N-gram dataset 22 (or N-gram corpus 23). For example, if an initial N-gram analysis using a first sequence A.B.C.D (e.g., corresponding to hypertension related health events) indicates that a second sequence A.B.C.D.E (e.g., where E corresponds to potential diabetes related health events given a condition of hypertension) occurs with high frequency in N-gram dataset 22, the analysis may predict that the individual may have a tendency to be potentially diagnosed with diabetes in the future.

Figure 8:
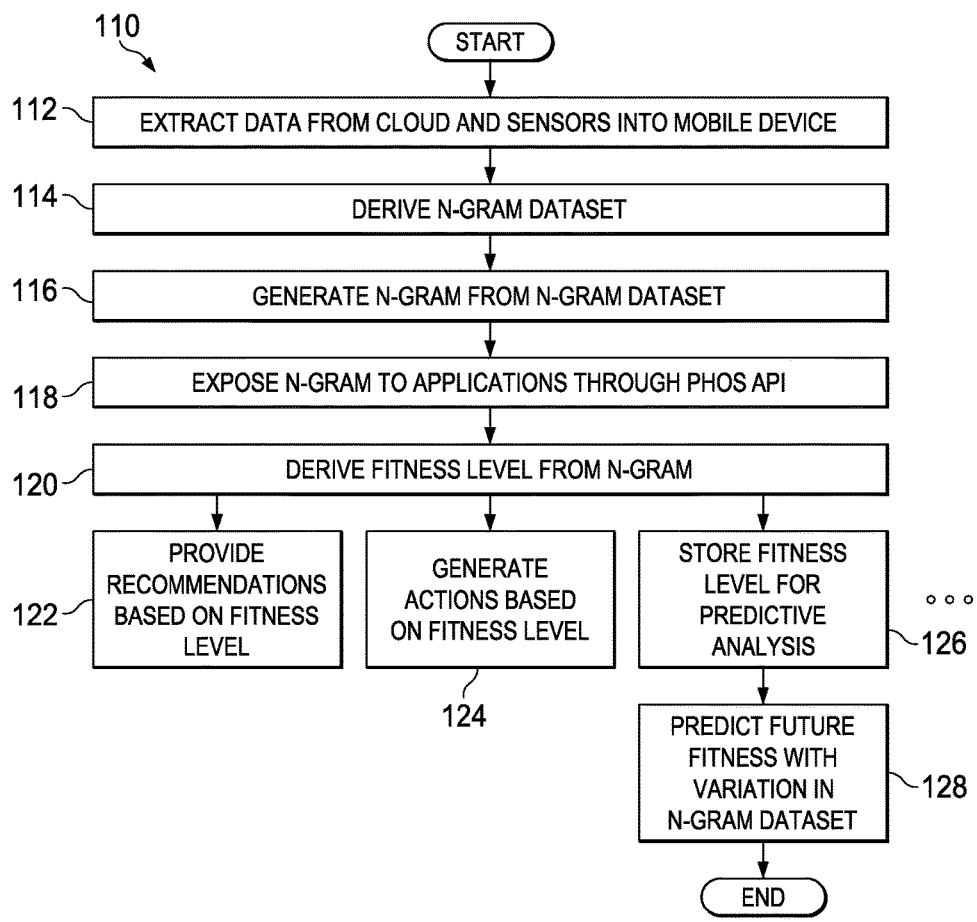
FIG. 8 is a simplified flow diagram illustrating example operations that may be associated with an embodiment of the system.

Turning to FIG. 8, FIG. 8 is a simplified flow diagram illustrating example operations 110 that may be associated with an embodiment of system 10. At 112, data (e.g., personal data 16, public data 18 and sensor data) may be extracted from cloud 14 and sensors into mobile device 12. At 114, dataset generate module 20 may derive N-gram dataset 22. At 116, N-gram generate module 26 may generate N-gram 28 from N-gram dataset 22. At 118, PHOS API 32 may expose N-gram 28 to applications 30. At 120, analysis module 34 may derive fitness from N-gram. Various actions may follow the analysis. For example, at 122, analysis module 34 may provide recommendations based on fitness. At 124, analysis module 34 may generate actions (e.g., alerting contact) based on fitness. At 126, the fitness may be stored for predictive analysis. At 128, future fitness based on variation in N-gram dataset 22 may be predicted. Various other operations may be performed by analysis module 34.

Figure 9:
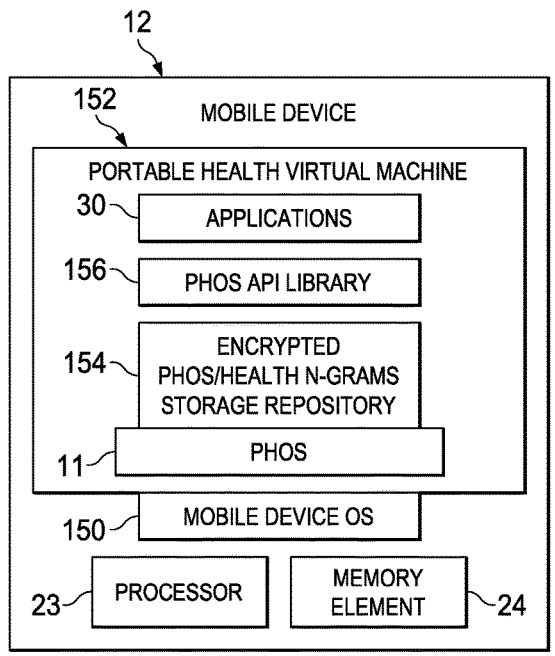
FIG. 9 is a simplified block diagram illustrating yet other example details of an embodiment of the system.

Turning to FIG. 9, FIG. 9 is a simplified block diagram illustrating example details of another embodiment of system 10. Mobile device 12, which includes processor 25 and memory element 24 may additionally comprise a mobile device operating system (OS) 150. In one example embodiment, mobile device OS 150 may comprise Android™ OS; in another example embodiment, mobile device OS 150 may comprise iPhone OS (iOS™); in yet another example embodiment, mobile device OS 150 may comprise Blackberry™ OS. Various other examples of mobile device OS may be included within the broad scope of the embodiments.

A portable health virtual machine 152 may execute on mobile device OS 150. In a general sense, a virtual machine (VM) is a software implementation of a computing device (e.g., personal computer, server, laptop, smartphone, etc.) that executes programs similar to the physical (e.g., corporeal) computing device. Example virtual machines include the Java virtual machine, Xen, Oracle® VM VirtualBox, just to name a few. In various embodiments, PHOS 11 may provide a suitable OS for operations (e.g., procedures, functions, processes, etc.) executing in (or by) portable health virtual machine 152. An encrypted PHOS/health N-Grams storage repository 154 and a PHOS API library 156 may be included in portable health virtual machine 152.

PHOS API library 156 may expose various API's to applications 30. In addition, PHOS API library 156 comprises a collection of implementations of behavior (e.g., written in terms of a computer language) that has a well-defined interface by which the behavior is invoked. In addition, the behavior is configured for reuse by multiple independent programs executing in PHOS 11. A specific program can invoke the library-provided behavior via a mechanism of the applicable language (e.g., PHOS API function calls). PHOS API library 156's code may be organized so that it can be used by multiple applications that have no connection to each other.

Encrypted PHOS/health N-grams storage repository 154 may comprise a repository of various health related data pertaining to the individual, including formatted data of N-gram dataset 22, N-gram 28, and other unformatted data comprising personal data 16, public data 18, and sensor data 19. Encrypted PHOS/health N-grams storage repository 154 may make the data therein available in an encrypted manner to applications 30 through API's. For example, getBloodPressure(DATE) operation from a particular application A may allow access to blood pressure data on the requested date (DATE) from encrypted PHOS/health N-grams storage repository 154. Because the data stored in encrypted PHOS/health N-grams storage repository 154 is encrypted, access to the repository through mechanisms outside the API or PHOS 11 may be ineffective, thereby providing data security.

Figure 10:
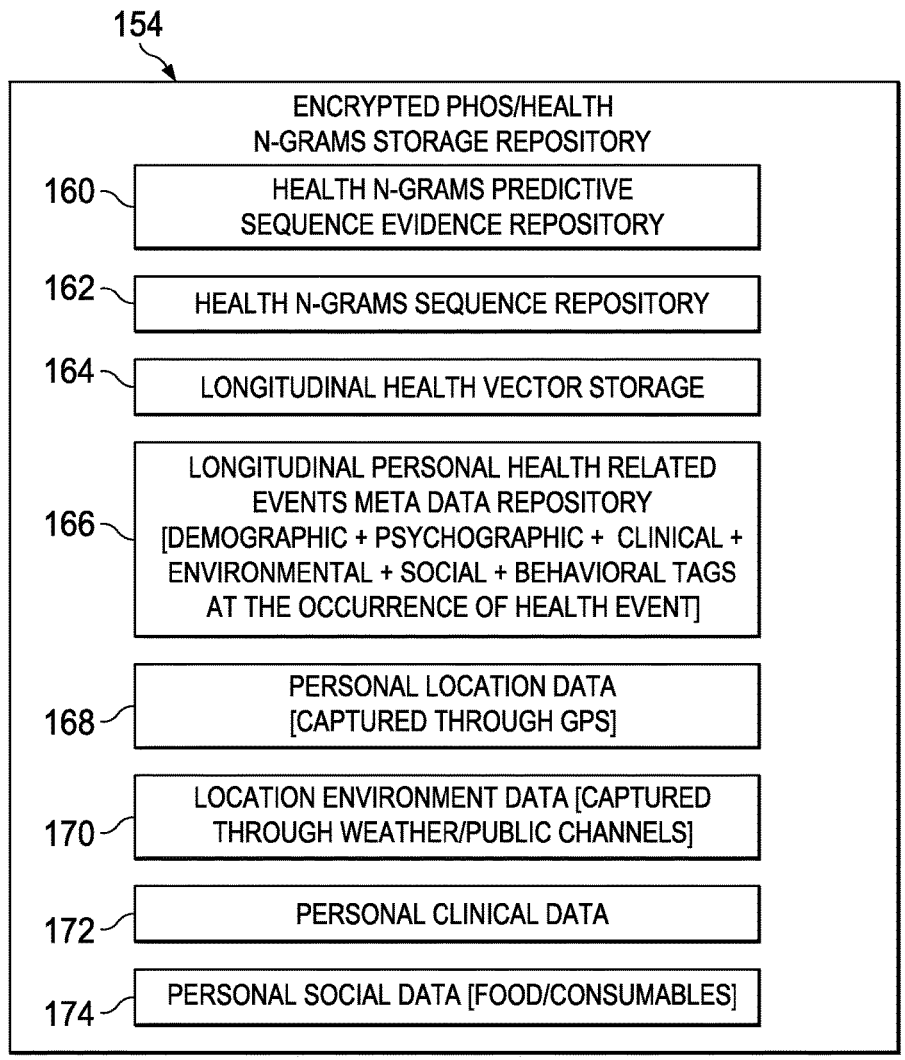
FIG. 10 is a simplified block diagram illustrating yet other example details of an embodiment of the system.

Turning to FIG. 10, FIG. 10 is a simplified block diagram illustrating example details of an embodiment of system 10. Encrypted PHOS/health N-grams storage repository 154 can include a N-grams predictive sequence evidence repository 160, a N-grams sequence repository 162, a longitudinal health vector storage 164, a longitudinal personal health related events meta data repository 166 (e.g., for storing demographic, psychographic, clinical, environmental, social and behavioral tags at occurrences of health events), a personal location data 168 (e.g., captured through GPS), a location environment data 170 (e.g., captured through weather/public channels), personal clinical data 172 (e.g., stored suitably), and personal social data 174 (e.g., food, consumables). In some embodiments, each element of encrypted PHOS/health N-grams storage repository 154 may comprise a separate database; in other embodiments, substantially all elements of encrypted PHOS/health N-grams storage repository 154 may comprise a single database, with appropriate fields and tags for ease of search and retrieval. Any suitable database, table, array, list, texts, tags and other storage mechanism may be used for encrypted PHOS/health N-Grams storage repository 154 within the broad scope of the embodiments.

Figure 11:
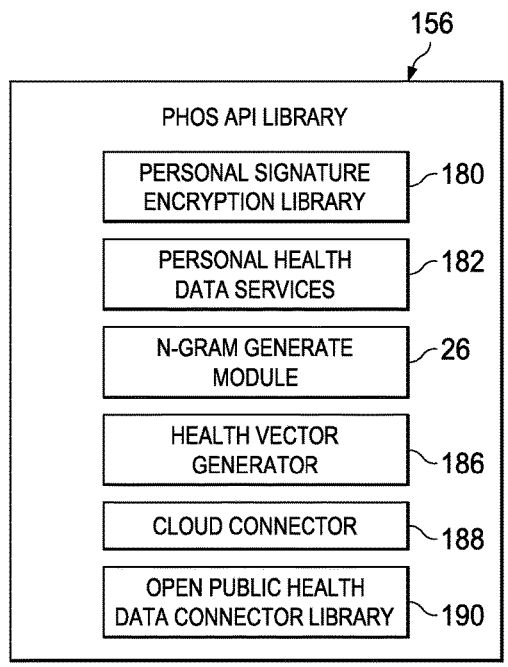
FIG. 11 is a simplified block diagram illustrating yet other example details of an embodiment of the system.

Turning to FIG. 11, FIG. 11 is a simplified block diagram illustrating example details of an embodiment of system 10. PHOS API library 156 may include a personal signature encryption library 180, a personal health data services 182, a health n-grams generator 184 (which can be the same or similar to n-gram generate module 26 of FIG. 1), a health vector generator 186, a cloud connector 188 and an open public health data connector library 190. In various embodiments, cloud connector 188 may comprise a software component embedded in, hosted on, or integrated with mobile device 12's networking functions to enable or enhance connectivity to cloud 14. In an example embodiment, cloud connector 188 can allow synchronization of data in mobile device 12 and cloud 14. Cloud connector 188 can also allow access for applications 30 to PHOS 11's metadata (e.g., N-gram 28, health vectors and other such data) through PHOS API 32, and enable its objects to be used suitably.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

In example implementations, at least some portions of the activities outlined herein may be implemented in software in, for example, PHOS 11. In some embodiments, one or more of these features may be implemented in hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, PHOS 11 described and shown herein (and/or its associated structures) may also include suitable interfaces for receiving, transmitting, and/or otherwise communicating data or information in a network environment. Additionally, some of the processors and memory elements associated with the various nodes may be removed, or otherwise consolidated such that a single processor and a single memory element are responsible for certain activities. In a general sense, the arrangements depicted in the FIGURES may be more logical in their representations, whereas a physical architecture may include various permutations, combinations, and/or hybrids of these elements. Moreover, if one embodiment comprises elements A, B, and C, and a second embodiment comprises elements B and D, then the inventive subject matter is also considered to include other remaining combinations of A, B, C, or D, even if not explicitly disclosed. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some of example embodiments, one or more memory elements (e.g., memory element 24) can store data used for the operations described herein. This includes the memory element being able to store instructions (e.g., software, logic, code, etc.) in non-transitory media such that the instructions are executed to carry out the activities described in this Specification.

A processor can execute any type of instructions associated with the data to achieve the operations detailed herein in this Specification. In one example, processors (e.g., processor 25) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, components in system 10 can include one or more memory elements (e.g., memory element 24) for storing information to be used in achieving operations as outlined herein. These devices may further keep information in any suitable type of non-transitory storage medium (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. The information being tracked, sent, received, or stored in system 10 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Note also that the disclosed subject matter herein enables construction or configuration of a mobile device to operate on digital data (e.g., raw sensor data, N-grams, etc.), beyond the capabilities of a human or unconfigured (e.g., off-the-shelf) mobile device. Although the digital data represents fitness or health states, it should be appreciated that the digital data is a representation of one or more digital models of fitness or health states and not the actual fitness or health states themselves, which comprise subjective experiences of a human being. By instantiation of such digital models in the memory of the mobile device, the mobile device is able to manage the digital models in a manner that could provide utility to an individual (e.g., a user of the mobile device) that the individual would lack without such a tool.

It should be noted that any language directed to a computer or computing device should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed herein with respect to the disclosed apparatus and operations. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods.

As used in the description herein and throughout the claims that follow, when a system, engine, server, device, module, or other computing element is described as configured to perform or execute functions on data in a memory, the meaning of "configured to" or "programmed to" refers to one or more processors or cores of the computing element being programmed by a set of software instructions stored in the memory of the computing element to execute the set of functions on target data or data objects stored in the memory.

One should appreciate that the disclosed techniques provide many advantageous technical effects including reduction in latency between a computing device ingesting healthcare data and generating a prediction or recommendation. Latency is reduced through storage of health care data in a memory and in the form of N-grams, which can be computationally analyzed quickly.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, system 10 may be applicable to other exchanges or routing protocols. Moreover, although system 10 has been illustrated with reference to particular elements and operations that facilitate the communication process, these elements, and operations may be replaced by any suitable architecture or process that achieves the intended functionality of system 10.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method, comprising:
   extracting data from a server via network communication into a mobile device, the mobile device comprising a memory element, a processor coupled with the memory element, and a portable health virtual machine executing on a mobile device operating system of the mobile device, the portable health virtual machine being a software implementation of a computing device that executes a personal health operating system (PHOS) using the processor and the memory element of the mobile device;
   generating, in the PHOS, an N-gram dataset from the data according to a data structure indicative and predictive of fitness of an individual, wherein the fitness comprises a numerical index representing a composite effect of various health conditions of the individual including interdependencies of the health conditions;
   generating an N-gram based on the N-gram dataset, the N-gram comprising a sequence of N grams where N is a positive integer, at least one of the grams having a value from a health record of the individual, the value being indicative of a health related event that affects a health condition of the individual;
   calculating the individual's fitness using the N-gram;
   performing, by either one or both of the mobile device and a remote device, an action based on the individual's fitness that was calculated using the N-gram;
   accessing an N-gram corpus of fitness-indicative data pertaining to a population via network communication between the mobile device and the server; and
   predicting a future medical diagnosis of the individual based on a frequency with which the N-gram occurs together with the medical diagnosis in the N-gram corpus.

2. The method of claim 1, further comprising exposing the N-gram to an application executing in the mobile device.

3. The method of claim 2, wherein the N-gram is exposed through a PHOS application programming interface (API).

4. The method of claim 3, wherein the application interacts through the PHOS API to obtain analysis results on the N-gram dataset using the N-gram.

5. The method of claim 4, further comprising generating an alert if the analysis results indicate a fitness change exceeding a preconfigured threshold.

6. The method of claim 1, further comprising analyzing the N-gram dataset using the N-gram for variation in fitness over time.

7. The method of claim 1, further comprising extracting data into the mobile device from a sensor.

8. The method of claim 1, further comprising providing a recommendation based on the fitness calculated from the N-gram.

9. The method of claim 1, further comprising generating an action based on the fitness calculated from the N-gram.

10. The method of claim 1, wherein the health related event is selected from the group consisting of: a diagnosis event, a testing event, an imaging event, an eating event, and a social event.

11. The method of claim 1, wherein the at least one of the grams comprises an attribute-value pair.

12. The method of claim 1, wherein said predicting the future medical diagnosis of the individual includes searching the N-gram corpus for an (N+1)-gram consisting of the N-gram in sequence with an additional gram having a value indicative of the medical diagnosis.

13. Non-transitory computer readable media that includes instructions for execution by a processor, and when executed by the processor is operable to perform operations comprising:
   extracting data from a server via network communication into a mobile device, the mobile device comprising a memory element, a processor coupled with the memory element, and a portable health virtual machine executing on a mobile device operating system of the mobile device, the portable health virtual machine being a software implementation of a computing device that executes a personal health operating system (PHOS) using the processor and the memory element of the mobile device;
   generating, in the PHOS, an N-gram dataset from the data according to a data structure indicative and predictive of fitness of an individual, wherein the fitness comprises a numerical index representing a composite effect of various health conditions of the individual including interdependencies of the health conditions;
   generating an N-gram based on the N-gram dataset, the N-gram comprising a sequence of N grams where N is a positive integer, at least one of the grams having a value from a health record of the individual, the value being indicative of a health related event that affects a health condition of the individual;
   calculating the individual's fitness using the N-gram;
   configuring either one or both of the mobile device and a remote device to perform an action based on the individual's fitness that was calculated using the N-gram;
   accessing an N-gram corpus of fitness-indicative data pertaining to a population via network communication between the mobile device and the server; and
   predicting a future medical diagnosis of the individual based on a frequency with which the N-gram occurs together with the medical diagnosis in the N-gram corpus.

14. The media of claim 13, wherein the operations further comprise exposing the N-gram to an application executing in the mobile device.

15. The media of claim 14, wherein the N-gram is exposed through a PHOS API.

16. The media of claim 15, wherein the application interacts through the PHOS API to obtain analysis results on the N-gram dataset using the N-gram.

17. The media of claim 13, wherein the health related event is selected from the group consisting of: a diagnosis event, a testing event, an imaging event, an eating event, and a social event.

18. The media of claim 13, wherein the at least one of the grams comprises an attribute-value pair.

19. A mobile device comprising:
   a memory element to store data;
   a processor, coupled with the memory element, to execute instructions associated with the data; and
   a portable health virtual machine executing on a mobile device operating system of the mobile device, the portable health virtual machine being a software implementation of a computing device that executes a personal health operating system (PHOS) using the processor and the memory element of the mobile device,
   wherein
   the processor and the memory element cooperate such that the mobile device is configured for:
      extracting data from a server via network communication into the mobile device;
      generating, in the PHOS, an N-gram dataset from the data according to a data structure indicative and predictive of fitness of an individual, wherein the fitness comprises a numerical index representing a composite effect of various health conditions of the individual including interdependencies of the health conditions;
      generating an N-gram based on the N-gram dataset, the N-gram comprising a sequence of N grams where N is a positive integer, at least one of the grams having a value from a health record of the individual, the value being indicative of a health related event that affects a health condition of the individual;
      calculating the individual's fitness using the N-gram;
      performing an action based on the individual's fitness that was calculated using the N-gram;
      accessing an N-gram corpus of fitness-indicative data pertaining to a population via network communication between the mobile device and the server; and
      predicting a future medical diagnosis of the individual based on a frequency with which the N-gram occurs together with the medical diagnosis in the N-gram corpus.

20. The mobile device of claim 19, further comprising an apparatus application executing in the mobile device, wherein the mobile device is further configured for exposing the N-gram to the application.

21. The mobile device of claim 20, wherein the N-gram is exposed through a PHOS API.

22. The mobile device of claim 21, wherein the application interacts through the PHOS API to obtain analysis results on the N-gram dataset using the N-gram.

23. The mobile device of claim 19, wherein the health related event is selected from the group consisting of: a diagnosis event, a testing event, an imaging event, an eating event, and a social event.

24. The mobile device of claim 19, wherein the at least one of the grams comprises an attribute-value pair.

* * * * *

UNITED STATES PATENT AND TRADEMARK OFFICE
CERTIFICATE OF CORRECTION

PATENT NO. : 10,262,759 B2
APPLICATION NO. : 14/657679
DATED : April 16, 2019
INVENTOR(S) : Patrick Soon-Shiong, Vasu Rangadass and Ravi Seshadri It is certified that error appears in the above-identified patent and that said Letters Patent is hereby corrected as shown below:

In the Claims

Claim 20, Line 2, "apparatus application" should be --application--

Signed and Sealed this
Twenty-eighth Day of May, 2019

Andrei Iancu
*Director of the United States Patent and Trademark Office*